(12) United States Patent
Dernoncourt et al.

(10) Patent No.: US 8,729,327 B2
(45) Date of Patent: *May 20, 2014

(54) PROCESS FOR COOLING THE STREAM LEAVING AN ETHYLBENZENE DEHYDROGENATION REACTOR

(71) Applicant: Total Petrochemicals France, Paris la Défense Cedex (FR)

(72) Inventors: Renaud Dernoncourt, Brussels (BE); Jean-Pierre Thoret Bauchet, Brussels (BE)

(73) Assignee: Total Research & Technology Feluy, Seneffe (Feluy) (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/868,755

(22) Filed: Apr. 23, 2013

(65) Prior Publication Data

US 2013/0303815 A1 Nov. 14, 2013

Related U.S. Application Data

(63) Continuation of application No. 12/477,683, filed as application No. PCT/EP2008/066023 on Nov. 21, 2008, now Pat. No. 8,450,547.

(30) Foreign Application Priority Data

Nov. 29, 2007 (EP) .................................... 07291441

(51) Int. Cl.
*C07C 5/327* (2006.01)

(52) U.S. Cl.
USPC ............................ 585/440; 585/441; 585/833

(58) Field of Classification Search
USPC .......................................... 585/440, 441, 833
See application file for complete search history.

(56) References Cited

U.S. PATENT DOCUMENTS 3,515,764 A * 6/1970 Ward et al. .................... 585/402

FOREIGN PATENT DOCUMENTS

TW 448151 B 8/2001

OTHER PUBLICATIONS

Taiwanese Office Action issued in Taiwanese Application No. 097142880 dated Aug. 23, 2013, and English translation thereof (16 pages).

* cited by examiner

*Primary Examiner* — Thuan D Dang

(57) ABSTRACT

The present invention is a process for the production of styrene monomer from ethylbenzene comprising the steps of:
a) catalytically dehydrogenating said ethylbenzene in the presence of steam thereby catalytically producing a dehydrogenation effluent gas containing essentially unreacted ethylbenzene, styrene monomer, hydrogen, steam and divinylbenzene;
b) quenching said effluent gas with an aqueous reflux in at least a quenching column to cool said effluent gas, and thereby obtaining a gas at the overhead and in the bottom a liquid stream warmer than the aqueous reflux;
c) condensing said overhead gas thereby producing a liquid organic phase, an aqueous phase and a gaseous phase;
d) using a portion or the whole of said aqueous phase of step c) as reflux for said step b) of quenching;
e) sending to a decanter the liquid stream obtained at step b) to recover an aqueous phase and an organic phase.

15 Claims, 2 Drawing Sheets

US 8,729,327 B2

PROCESS FOR COOLING THE STREAM LEAVING AN ETHYLBENZENE DEHYDROGENATION REACTOR

CROSS-REFERENCE TO RELATED APPLICATIONS

This application is a Continuation of U.S. application Ser. No. 12/744,683, filed on Nov. 23, 2010, which claims the benefit of PCT/EP2008/066023, filed on Nov. 21, 2008, which claims priority from EP 07291441.9, filed on Nov. 29, 2007.

FIELD OF THE INVENTION

The present invention relates to a process for cooling the stream leaving an ethylbenzene dehydrogenation reactor. The catalytic dehydrogenation of ethylbenzene to produce styrene is typically carried out at temperatures within the range of about 540-660° C. under near atmospheric or even subatmospheric pressure conditions. Typically, an ethylbenzene steam feed having a steam to ethylbenzene mole ratio of perhaps 6, 7 or 8 or even higher is passed over a dehydrogenation catalyst such as iron oxide in an adiabatic dehydrogenation reactor. Large quantities of steam are employed in order to supply a part of the sensible heat to the dehydrogenation (endothermic reaction), to reduce the partial pressure of the ethyl benzene to favor the dehydrogenation reaction, and to keep the catalyst free of coke and carbon deposits. The stream (also called the effluent gas) leaving the ethylbenzene dehydrogenation reactor contains primarily styrene, hydrogen, unreacted ethylbenzene, benzene, toluene and small amounts of divinylbenzene, methane, ethane, carbon monoxide, carbon dioxide, various polymeric materials and tars as well as an aqueous component.

BACKGROUND OF THE INVENTION

U.S. Pat. No. 3,256,355 relates to the dehydrogenation of ethylbenzene to make styrene. In said prior art, referring to the stream leaving the ethylbenzene dehydrogenation reactor, the latent heat of condensation of the contained steam is used to heat the reboilers of distillation columns in the overall process. Said stream is firstly washed with hot water to remove tars, then compressed and sent to the reboilers.

U.S. Pat. No. 4,288,234 describes an ethylbenzene dehydrogenation wherein the stream leaving the ethylbenzene dehydrogenation reactor is introduced in a cooling zone containing one or more cooling steps and a compression step. The remaining gases, essentially hydrogen, are washed with ethylbenzene and then polyethylbenzene to remove aromatics.

U.S. Pat. No. 4,628,136 describes an ethylbenzene dehydrogenation wherein the stream leaving the ethylbenzene dehydrogenation reactor is introduced in a conventional cooling zone where are recovered (i) a gaseous phase (essentially hydrogen), (ii) an organic phase (ethylbenzene and styrene) and (iii) an aqueous phase. Said aqueous phase is further mixed with fresh ethylbenzene then is vaporized while condensing the reflux of the ethylbenzene/styrene distillation column and then sent to the dehydrogenation catalyst.

U.S. Pat. No. 6,388,155 relates to a process for the production of styrene monomer from ethylbenzene comprising the steps of:
a) catalytically dehydrogenating said ethylbenzene in the presence of steam thereby catalytically producing a dehydrogenation effluent gas containing unreacted ethylbenzene and lighter components and styrene monomer and heavier components;
b) scrubbing said effluent gas with reflux to remove at least a portion of said styrene monomer and heavier components from said effluent gas;
c) condensing said scrubbed effluent gas thereby producing a liquid organic dehydrogenation mixture, an aqueous phase and a gaseous phase; and
d) using a portion of said liquid organic dehydrogenation mixture as said reflux for said step b) of scrubbing.

In the bottoms of said scrubber of step b) an aqueous phase and an organic phase are recovered, said aqueous phase is mixed with aqueous phase recovered at step c) and said organic phase is fed to a distillation column for separation of the ethylbenzene and styrene monomer.

It has been discovered a new process wherein the dehydrogenation effluent of step a):
is quenched with an aqueous phase and
essentially all the steam present in the ethylbenzene dehydrogenation effluent stream is recovered in the bottom of the quench column.

One advantage is that most of the divinylbenzene and polymerics materials contained in said dehydrogenation effluent are easily removed. Said removal eliminates the fouling and plugging problems in condensers and other apparatus in the course of styrene recovering.

U.S. Pat. No. 3,515,764, GB 2 092 U.S. Pat. No. 3,515,764,018, U.S. Pat. No. 3,515,765, U.S. Pat. No. 3,515,766 and U.S. Pat. No. 3,515,767 have described processes for recovering styrene in an ethylbenzene dehydrogenation effluent stream. In said prior arts the quenching apparatus has only an overhead effluent.

BRIEF DESCRIPTION OF THE INVENTION

The present invention is a process for the production of styrene monomer from ethylbenzene comprising the steps of:
a) catalytically dehydrogenating said ethylbenzene in the presence of steam thereby catalytically producing a dehydrogenation effluent gas containing essentially unreacted ethylbenzene, styrene monomer, hydrogen, steam and divinylbenzene;
b) quenching said effluent gas with an aqueous reflux in at least a quenching column to cool said effluent gas, and thereby obtaining a gas at the overhead and in the bottom a liquid stream warmer than the aqueous reflux;
c) condensing said overhead gas thereby producing a liquid organic phase, an aqueous phase and a gaseous phase;
d) using a portion or the whole of said aqueous phase of step c) as reflux for said step b) of quenching;
e) sending to a decanter the liquid stream obtained at step b) to recover an aqueous phase and an organic phase.

Styrene is recovered from organic phases of steps c) and e) by known means.

An advantage is that most of the divinylbenzene and polymerics materials contained in said dehydrogenation effluent are removed. Said removal eliminates the fouling and plugging problems in condenser(s) of step c).

According to a specific embodiment a mixing tank is inserted on the liquid stream between the quenching column and the decanter of step e). In said mixing tank is introduced an effective amount of an aromatic component (advantageously an aromatic component which cannot polymerize), advantageously ethylbenzene or benzene or toluene or mixture thereof. Purpose of said introduction is to cause the migration of organic heavies to the organic phase in the decanter which leads to a clean aqueous phase leaving the decanter. "Clean aqueous phase" means that said aqueous phase leaving the decanter will not induce fouling or random polymerizations in the vessels, pipes and any piece of equipment.

According to another specific embodiment the aqueous phase leaving the decanter of step e) goes through a stripper to remove a substantial part of any remaining organic component, mainly ethylbenzene and benzene or toluene. Advantageously as much as possible as the remaining organic components are to be removed. Then said aqueous phase is advantageously used to make steam.

According to another specific embodiment relating to the quenching column of step b), the aqueous phase from step c) is sent to the top of said quenching column and the dehydrogenation effluent from step a) is sent to the lower end of said quenching column. According to another specific embodiment said aqueous phase from step c) is dispersed in the quenching column by spray nozzles.

According to another specific embodiment said quenching column has no liquid level in the bottoms in order to reduce the residence time to prevent fouling and random polymerizations.

DETAILED DESCRIPTION OF THE INVENTION

Figure 1:
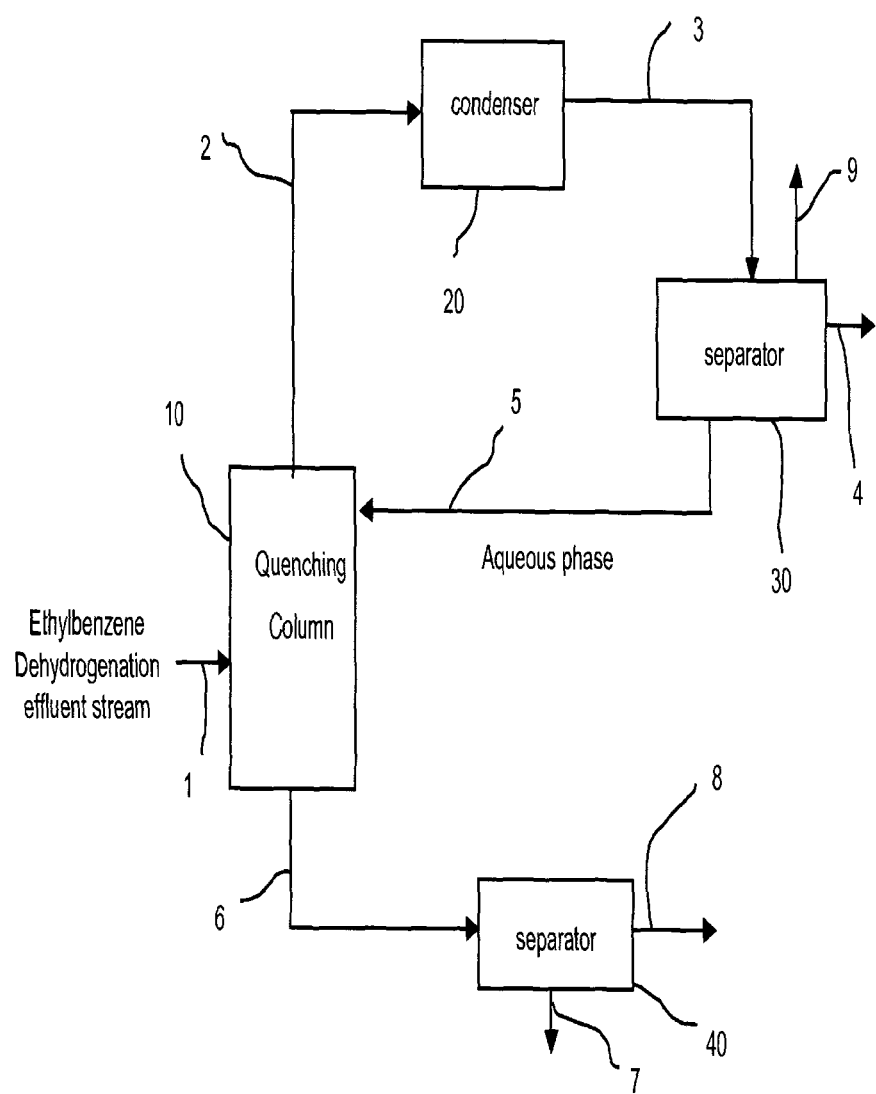
FIG. 1 depicts a system for cooling a stream leaving an ethylbenzene dehydrogenation reactor in accordance with at least one embodiment of the present disclosure.
Figure 2:
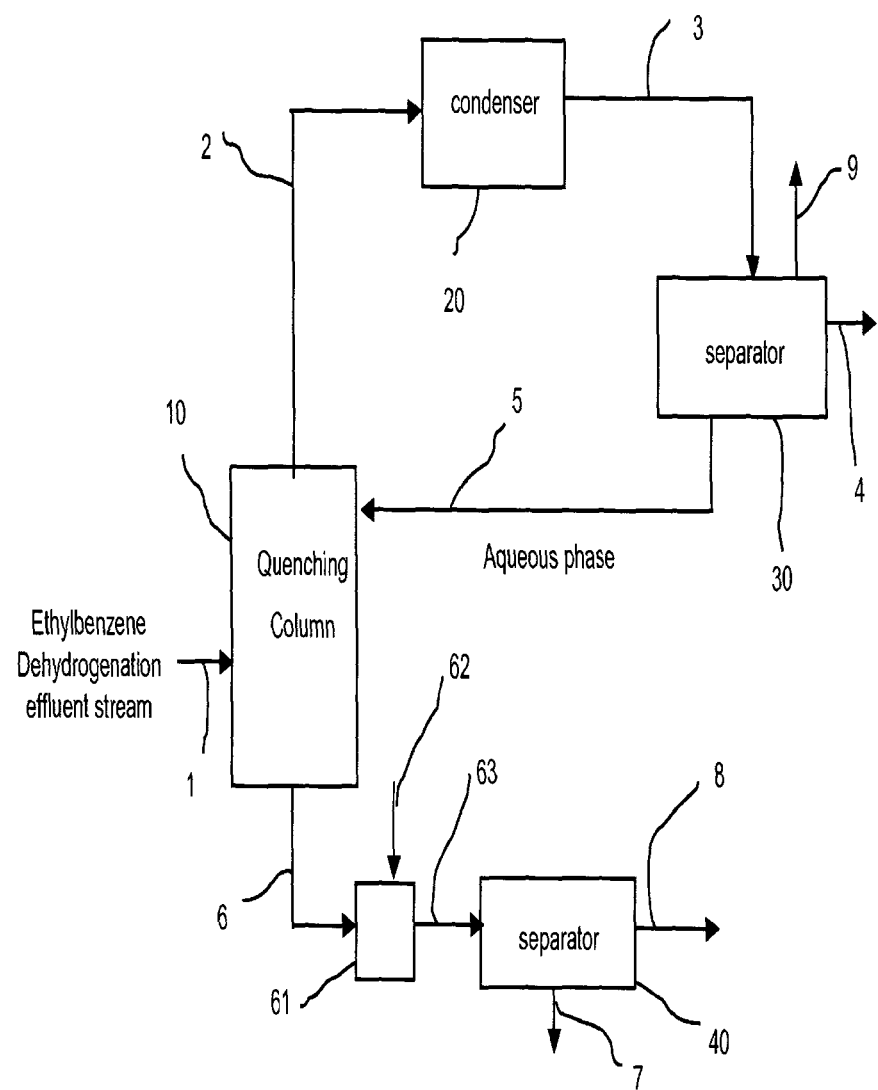
FIG. 2 depicts a system for cooling a stream leaving an ethylbenzene dehydrogenation reactor in accordance with at least one embodiment of the present disclosure.

FIG. 1 illustrates a process according to the invention. 10 is the quenching column of step b), 20 is the condenser of step c), 30 is a decanter (separator) and 40 the decanter of step e). The stream leaving the ethylbenzene dehydrogenation reactor is cooled at about 120-150° C. and sent via line 1 to the quenching column 10. The quenching column is fed via line 5 by an aqueous phase at about 40° C. The liquid stream 6 leaving the quenching column is at about 65° C., the quenching column overhead gas is at about 70° C. and is sent via line 2 to a condenser 20. The condensed and uncondensed components leaving the condenser 20 at about 40° C. are sent via line 3 to a decanter 30 producing a gaseous stream 9, a liquid organic phase 4 and an aqueous phase 5. The stream 6 leaving the quenching column 10 is sent to a decanter 40 to produce a liquid organic phase 8 and an aqueous phase 7. Optionally a mixing tank (not shown on this FIG. 1) is inserted on stream 6, In said mixing tank is introduced an effective amount of an aromatic component, advantageously ethylbenzene or benzene or toluene or mixture thereof. FIG. 2 derives from FIG. 1 by insertion of the mixing tank on stream 6. Stream 6 leaves the quenching column and is sent to the mixing tank 61 wherein an aromatic component is introduced by line 62 and is sent via line 63 to the decanter 40 of step c).

As regards the stream (also called the effluent gas) leaving the ethylbenzene dehydrogenation reactor, it contains primarily styrene, hydrogen, unreacted ethylbenzene, benzene, toluene and small amounts of divinylbenzene, methane, ethane, carbon monoxide, carbon dioxide, various polymeric materials and tars as well as an aqueous component. Advantageously the stream leaving the ethylbenzene dehydrogenation reactor is available at a reduced pressure and the quenching column is operating at said reduced pressure. By way of example this reduced pressure is in the range 0.2 to 0.7 bar absolute, advantageously in the range 0.3 to 0.5.

As regards the quenching column of step b), it can be any type of liquid/gas contactor such as, by way of example, a packed column or a column with trays or a combination of trays and packing. Advantageously the aqueous phase sent on top of the quenching column is dispersed by spray nozzles and there is no packing. Optionally one or more (advantageously two) washing trays can be located on top of the quenching column above the spray nozzles but they have to be fed with a part of the aqueous phase sent to the spray nozzles.

The liquid organic phases recovered at step c) and at step e) are sent to a recovery section to separate styrene and ethylbenzene from all impurities, ethylbenzene is recycled to the dehydrogenation.

According to a specific embodiment a mixing tank is inserted on the liquid stream between the quenching column and the decanter of step e). In said mixing tank is introduced an effective amount of an aromatic component, advantageously ethylbenzene or benzene or toluene or mixture thereof. Purpose of said introduction is to cause the migration of organic heavies to the organic phase in the decanter which leads to a clean aqueous phase leaving the decanter. "Clean aqueous phase" means that said aqueous phase leaving the decanter will not induce fouling or random polymerizations in the vessels, pipes and any piece of equipment. The aromatic component introduced in the mixing tank can be any aromatic which cannot polymerize, advantageously it is ethylbenzene or benzene or toluene or mixture thereof. Amount of said aromatic component introduced is 0.05 to 5% by weight of the amount of the aqueous phase. Volume of said mixing tank is designed to have advantageously a residence time of 5 to 45 minutes.

According to another specific embodiment the aqueous phase leaving the decanter of step e) goes through a stripper to remove as much as possible any remaining organic component, mainly ethylbenzene and benzene or toluene. Then said aqueous phase is advantageously used to make steam. Said stripper is known per se and works like any stripper (exhausting section of a distillation column). Advantageously the temperature of the top of the stripper is around 95° C. to 110° C. depending on the operating pressure of the stripper. Overhead of the stripper comprises water, benzene, toluene and other aromatics, is condensed and sent advantageously to a decanter, the organic phase being sent to the recovery section that separates styrene, ethylbenzene, and other impurities. Advantage of the quenching column of the invention is the energy savings in heating of said aqueous phase to be stripped

The invention claimed is:

1. A process for the production of styrene monomer from ethylbenzene, comprising:
    catalytically dehydrogenating ethylbenzene in the presence of steam thereby catalytically producing a dehydrogenation effluent gas comprising unreacted ethylbenzene, styrene monomer, hydrogen, steam, polymeric materials, and divinylbenzene;
    quenching the dehydrogenation effluent gas with an aqueous reflux in at least one quenching column comprising to cool the dehydrogenation effluent gas, thereby producing a gaseous overhead stream and a liquid bottom stream containing most of the divinylbenzene and polymeric materials in the dehydrogenation effluent gas, wherein the liquid bottom stream has a temperature greater than the aqueous reflux;
    condensing the gaseous overhead stream, thereby producing a liquid organic phase, a first aqueous phase and a gaseous phase;

recycling at least a portion of the first aqueous phase to the aqueous reflux; and sending the liquid bottom stream to a decanter to recover a second aqueous phase which is used is make the steam for the dehydrogenation step, and an organic phase;

wherein the gaseous overhead stream and the liquid bottom stream exit the quenching column via separate lines.

2. The process of claim 1, wherein the liquid bottom stream exits the quenching column below a point that the gaseous overhead stream exits the quenching column.

3. The process of claim 1, further comprising recovering styrene from the liquid organic phase and the organic phase.

4. The process of claim 1, wherein the liquid bottom stream is first sent to a mixing tank prior to being sent to the decanter.

5. The process of claim 4, wherein an effective amount of an aromatic component is introduced into the mixing tank in an amount effective to cause the migration of organic heavies to the organic phase in the decanter.

6. The process of claim 5, wherein the effective amount of the aromatic component introduced is from 0.05 to 5 wt. % by weight of the second aqueous phase.

7. The process of claim 5, wherein the aromatic component is an aromatic component that cannot polymerize.

8. The process of claim 1, wherein the second aqueous phase leaving the decanter is sent to a stripper.

9. The process of claim 1, wherein the aqueous reflux is sent to a top of the quenching column and the dehydrogenation effluent gas is sent to a lower end of the quenching column.

10. The process of claim 1, wherein the quenching column has no liquid level in a lower end thereof.

11. The process of claim 1, wherein the aqueous reflux is dispersed in the quenching column by spray nozzles.

12. The process of claim 11, wherein one or more washing trays are located at a top of the quenching column above the spray nozzles and are contacted with at least part of the aqueous reflux sent to the spray nozzles.

13. The process of claim 1, wherein the quenching column is operated under pressures ranging from 0.2 to 0.7 bar absolute.

14. The process of claim 1, wherein quenching column is a liquid/gas contactor.

15. The process of claim 1, wherein the quenching column is a selected from a group consisting of a packed column, a column comprising trays, and a column comprising trays and packing.

* * * * *